(12) United States Patent
Doerries et al.

(10) Patent No.: US 6,355,794 B1
(45) Date of Patent: Mar. 12, 2002

(54) LACTAM DERIVATIVES FOR MELAMINE IMPREGNATING RESINS, AND RESIN MIXTURES CONTAINING THEM

(75) Inventors: Peter Doerries, Frankfurt am Main; Johann Wonner, Offenbach, both of (DE)

(73) Assignee: Solutia Germany GmbH & Co. KG, Mainz-Kastel (DE)

( * ) Notice: Subject to any disclaimer, the term of this patent is extended or adjusted under 35 U.S.C. 154(b) by 0 days.

(21) Appl. No.: 09/166,222

(22) Filed: Oct. 5, 1998

(30) Foreign Application Priority Data

Oct. 10, 1997 (DE) .......................... 197 44 942

(51) Int. Cl.⁷ ................. C07D 223/10; C07D 201/00; C07D 201/02
(52) U.S. Cl. .................. 540/531; 540/533; 540/534
(58) Field of Search ............... 540/531, 533, 540/534

(56) References Cited

U.S. PATENT DOCUMENTS

| | | | |
|---|---|---|---|
| 3,823,160 A | * 7/1974 | Smith et al. | 260/326.5 |
| 3,853,910 A | 12/1974 | Freyermuth et al. | 260/326.5 |
| 4,185,017 A | 1/1980 | Piesch et al. | 260/239.3 |
| 4,760,152 A | 7/1988 | Tracy et al. | 548/551 |
| 4,769,454 A | 9/1988 | Blank et al. | 540/531 |

FOREIGN PATENT DOCUMENTS

| | | |
|---|---|---|
| DE | 21 14 295 A | 10/1971 |
| DE | 23 28 431 A | 1/1975 |
| DE | 26 16 374 | 4/1976 |
| DE | 26 16 374 A | 10/1977 |
| DE | 26 37 424 A | 2/1978 |
| DE | 27 55 588 A | 6/1979 |
| DE | 27 55 589 A | 6/1979 |
| DE | 35 06 473 | 2/1985 |
| DE | 35 06 473 A | 8/1986 |
| DE | 37 00 451 | 1/1987 |
| EP | 0 275 551 | 12/1987 |
| EP | 0 275 551 A | 7/1988 |
| EP | 0747531 A | 12/1996 |
| FR | 1 546 430 A | 10/1968 |
| FR | 2 481 299 A | 10/1981 |
| GB | 1464014 | 2/1977 |
| GB | 1 547 333 | 4/1977 |
| GB | 1547333 | 6/1979 |

OTHER PUBLICATIONS

Chauzov et al.; Journal of General Chemistry of the USSR; 59 (1989); p. 425.

Kunststoff–Handbuch; 2nd Edition; vol. 10; 1988; pp. 41 to 49.

* cited by examiner

Primary Examiner—Bruck Kifle
Assistant Examiner—Hong Liu
(74) Attorney, Agent, or Firm—Foley & Lardner

(57) ABSTRACT

N-Alkoxymethylactams are obtained by reacting lactams with formaldehyde and hydroxyl-containing compounds selected from diol monoethers. The substituted lactams are useful as an additive to melamne impregnating resings.

4 Claims, No Drawings

LACTAM DERIVATIVES FOR MELAMINE IMPREGNATING RESINS, AND RESIN MIXTURES CONTAINING THEM

BACKGROUND OF THE INVENTION

1. Field of the Invention

The present invention relates to lactam derivatives, methods for their production, and methods for their use.

2. Description of Related Art

The preparation of various reaction products of $\epsilon$-caprolactam, formaldehyde, and hydroxyl-containing compounds is known: for example, N-[(isopentyloxy)methyl]caprolactam from V. A. Chauzov et al., Journal of General Chemistry of the USSR, 59 (1989) p. 425; and N-[(2,6-di-tert-butylphenoxy)methyl]caprolactam from DE-A 26 16 374. The preparation of N,N-linked bislactam compounds is described in DE-A 35 06 473; the preparation of N-methylolcaprolactam in DE-A 37 00 451.

Melamine resins made from melamine and formaldehyde are general knowledge and are described, for example, in "Kunststoff-Handbuch", 2nd edition, 1988, vol. 10, pp. 41 to 49. Melamine-formaldehyde precondensates whose methylol groups are unetherified or etherified in part with alcohols such as methanol are generally prepared in an aqueous medium and also commercialized in aqueous form. They are used preferably for impregnating paper webs, especially decorative paper webs, which are subsequently employed to produce laminates, decoratively coated chipboard panels or compression-formed laminates. For this purpose, the paper webs are impregnated to a defined resin content in the aqueous impregnating-resin solutions, to which a curing agent may have been added, and are dried to a defined residual moisture content at temperatures from 120 to 200° C. The fabric or paper webs treated in this way are pressed onto woodbase materials or a stack of resinated papers employing pressures of from 0.8 to 12 MPa (from 8 to 120 bar) and temperatures of from 100 to 180 C.

In this way, decorative laminates and coated woodbase materials are obtained which are employed primarily in interior furnishing, for producing furniture or as a floor covering, to cite but a few of the possible applications.

Melamine resins are prepared by condensing formaldehyde with melamine, the condensation being continued only to a point at which the reaction products are still soluble and meltable. When this point is reached, the condensation is terminated by cooling and by establishing a weakly alkaline pH. This gives products which have not been fully condensed, these products also being termed melamine resin precondensates and being used in the form of their aqueous solutions, for example, as impregnating resins. It is also now possible to replace up to 20% of the melamine by one or more other amino resin formers, examples being guanamines (e.g., acetoguanamine, benzoguanamine and caprinoguan-amine), dicyandiamide, urea and thiourea, and also cyclic ureas (e.g. ethylene- and propyleneurea).

When the fabric or paper webs which have been impregnated with impregnating resin and dried are pressed into laminates, curing takes place as a result of thorough crosslinking of the condensate. When coating woodbase materials in particular it is important that the melamine resins employed are elasticized with modifiers in order to prevent subsequent cracking of the coated surface. The impregnating resin can be etherified in part with lower alcohols or modified with modifiers such as polyhydric alcohols, carboxamides, glycols, sulfonamides and sugars, and can also be catalyzed with acidic inorganic or organic salts.

In the art, diethylene glycol and $\epsilon$-caprolactam are frequently employed as modifiers. They give the cured films the necessary elasticity coupled with good surface properties, such as low soiling tendency, low sensitivity to steam and boiling water, low yellowing propensity, high scratch resistance, low propensity to cracking, and good postforming properties.

A disadvantage of these modifiers is their relatively high volatility. When papers impregnated with resins modified in this way are dried, some of the modifiers present are given off into the air. This problem is exacerbated when the dryer temperatures are raised owing to higher machine speeds. In accordance with the art, customary drying temperatures are from 140 to 200° C. In order to avoid these emissions, it is therefore necessary with prior art resins to make considerable investment in filter units and/or post-combustion units, in general.

This problem applies in particular to $\epsilon$-caprolactam, for which a MAC level of 5 mg/m$^3$ has been laid down.

SUMMARY OF THE INVENTION

It is therefore an object of the present invention to provide modifiers for impregnating resins and resins modified therewith which when used in the coating of woodbase materials result in minimal amounts of organic compounds being emitted. In addition, the coatings produced with these resins should be elastic and should not tend to crack.

It is also an object of the invention to provide methods of making and using such modifiers.

In accordance with these and other objectives, there has been provided in accordance with the present invention an N-alkoxymethyllactam of the formula VI

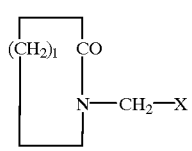

(VI)

where X is $-(OCH_2-CR^1H)_m-OR^2$, and $R^1$ and $R^2$ in each case independently of one another are hydrogen or a linear or branched alkyl radical having 1 to 6 carbon atoms, l is 3 to 12 and m is 1 to 20, or where X is $-O-(CH_2)_n-OR^3$, and $R^3$ is hydrogen or a linear or branched alkyl radical having 1 to 6 carbon atoms and n is 2 to 8, obtained by reacting a lactam of the formula I

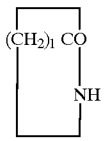
(I)

where 1 is as defined above, with formaldehyde and hydroxyl-containing compounds selected from diols and/or diol monoethers of formula II

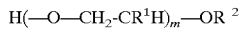
(II), where $R^1$, $R^2$ and m are as defined above, and diols and/or diol monoethers of formula III

(III)

where $R^3$ and n are as defined above, wherein the reaction comprises reacting from 1 to 4 mol of formaldehyde and from 0.5 to 6 mol of the hydroxy containing compound one another per mole of the lactam of the formula I.

In accordance with these and other objectives, there has also been provided a is a mixture comprising one or more N-alkoxymethyllactams of the formula VI

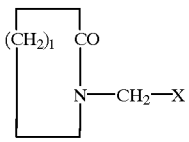
(VI)

and one or more N-methylollactams of the formula IV

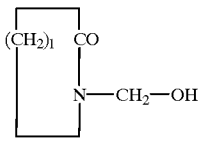
(IV)

and one or more N, N'-methylenebislactams of the formula V

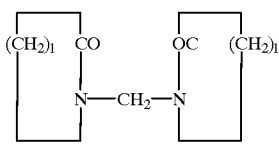
(V)

in which X is $-(OCH_2-CR^1H)_m-OR^2$ or $-O-(CH_2)_n-OR^3$, $R^1$, $R^2$ and $R^3$ independently of one another are hydrogen or a linear or branched alkyl radical having 1 to 6 carbon atoms and l is an integer from 3 to 12, m is 1 to 20, and n is 2 to 8.

In accordance with these and other objectives, there has been provided a melamine impregnating resin formulation comprising or prepared from an N-alkoxymethyllactam of the formula VI as modifier in a proportion by mass of from 1 to 20%, based on the mass of the solid melamine resin.

In accordance with these and other objectives, there has been provided a melamine impregnating resin formulation comprising or prepared from and a mixture as discussed above as modifier in a proportion by mass of from 1 to 20%, based on the mass of the solid melamine resin.

Further objects, features, and advantages of the invention will become apparent from the detailed description that follows.

DETAILED DESCRIPTION OF PREFERRED EMBODIMENTS

It has now been found that the disadvantages of the use of prior art modifiers can be avoided if the modifier employed comprises reaction products of lactams of the formula I

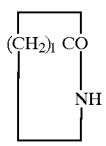
(I)

in which l is from 3 to 12, preferably 3, 4, 5 or 11 and, with particular preference, is 5 (caprolactam) and 11 (laurolactam) with formaldehyde and diols and/or diol monoethers of the formula II

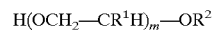
(II)

in which $R^1$ and $R^2$ are hydrogen or a linear or branched alkyl radical having 1 to 6, preferably 1 to 4 and, with particular preference, 1 or 2 carbon atoms and m is from 1 to 20, preferably from 2 to 4 or with diols and/or diol monoethers of the formula III

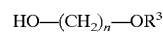
(III)

in which $R^3$ is hydrogen or a linear or branched alkyl radical having 1 to 6, preferably 1 to 4 and, with particular preference, 1 or 2 carbon atoms and n is from 2 to 8, preferably from 2 to 4.

It is also useful in accordance with the invention to employ mixtures of different lactams; similarly, mixtures of the diols or diol monoethers of the formulae II and III, respectively, can also be employed.

The N-alkoxymethyllactams may be prepared as desired. In one process the molar ratio of the precursors (starting materials) is chosen so that from 1 to 4 mol of formaldehyde and from 0.5 to 6 mol of the diol and/or of the diol monoether of the formula II and/or from 0.5 to 6 mol of the diol and/or of the diol monoether of the formula HII are reacted with one another per mole of the lactam of the formula I. If the diol and/or the diol monoether of the formula II and/or of the formula III is employed in excess for reaction with the lactam of the formula I, then it is additionally effective as a solvent.

The reaction between the lactam of the formula I, formaldehyde and the diol and/or diol monoether of the formula II and/or of the formula III generally takes place at temperatures between 50 and 200° C., preferably between 80 and 140° C., in the presence of known water-eliminating catalysts, preferably of an acidic catalyst. Any desired catalysts can be used. Examples of suitable acidic catalysts include inorganic acids or strong organic acids, such as sulfamic acid, phosphoric acid, hydrochloric acid, nitric acid, sulfuric acid, formic acid, oxalic acid, benzenesulfonic acid, or toluenesulfonic acid, and also acidic salts, such as alkali metal hydrogen sulfates.

It is also useful to carry out the reaction between the lactam of the formula I, formaldehyde and the diol and/or diol monoether of the formula II and/or of the formula III in two stages: in the first stage initially in the presence of alkaline inorganic or organic compounds, such as alkali metal hydroxides, alkali metal carbonates or alkaline earth metal carbonates, and also amines, the lactam I and formaldehyde are reacted with one another at temperatures between 50 and 200° C., preferably between 80 and 120° C., in the abovementioned molar ratio. In this stage, the lactam of the formula I is methylolated. Subsequent condensation then takes place in the second stage in the presence of known water-eliminating catalysts, preferably of an acidic catalyst. Suitable acidic catalysts are the abovementioned inorganic and strong organic acids.

In order to bring the reaction to completion it is useful, during the reaction or thereafter, to distill off the water of the reaction, at atmospheric or reduced pressure. In this context, the condensation reaction can also be conducted in the presence of water-immiscible solvents, preferably inert aromatic hydrocarbons, which are able to form an azeotrope with water. The use of inert aromatic hydrocarbons as solvents for the reaction is particularly advantageous when formaldehyde is employed in the form of aqueous formaldehyde solutions, since in that case the removal of the entrained water is promoted by azeotropic distillation. The water can in this case be removed substantially or completely from the product mixture by azeotropic distillation, with the solvent possibly being recycled in a known manner following phase separation from the water.

The formaldehyde can be employed in the form of an aqueous solution, preferably a solution with a concentration of more than 30%, or in the form of a solution of formaldehyde gas in the diol or diol monoether of the formula II or III employed in the reaction, or else in a low-boiling alcohol. Preferably, however, the formaldehyde is supplied to the reaction in the form of paraformaldehyde. Where aqueous solutions of formaldehyde or solutions in low-boiling alcohols are employed, it should be ensured that the water or lower alcohol introduced with the formaldehyde solution is able to distill off from the reaction mixture, which is promoted in particular, in the presence of water, by adding an organic solvent which forms an azeotropic mixture with the water. Where paraformaldehyde is employed as the formaldehyde source, the distillative removal of the water of the reaction can be omitted.

The reaction products obtainable by the process of the invention are mixtures of different lactam derivatives. In the course of the reaction, the lactam in the formula I reacts with the formaldehyde to form N-methylollactams of the formula IV,

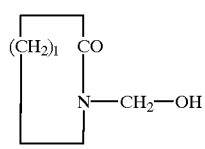

N,N'-methylenebislactams of the formula V

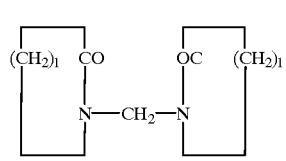

and, with the formaldehyde and the diol and/or diol monoether of the formula II and/or with the diol of the formula III employed, to give novel condensation products of the formula VI

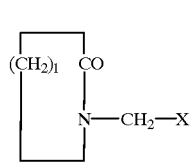

in which X is —(OCH$_2$—CR$^1$H)$_m$—OR$^2$
and R$^1$, R$^2$, l and m are as defined above or
in which X is —O—(CH$_2$)$_n$—OR$^3$
and R$^3$, l and n are as defined above.

The lactam derivatives of the formula VI obtainable by the process of the invention have not been described previously; they are likewise provided by the present invention.

The mixtures obtainable in accordance with the process of the invention can include any desired proportions of components, and generally include proportions by mass of from 5 to 50%, preferably from 10 to 45%, of N-alkoxymethyllactams of the formula VI, from 30 to 80%, preferably from 35 to 75%, of N,N'-methylenebislactams of the formula V and from 0 to 5%, preferably less than 2%, of unreacted lactams of the formula I; the remainder to 100% (i. e. from 0 to 65%, preferably from 5 to 60%) is N-methylol-lactam of the formula IV.

Any desired lactams of formula (I) and components of formula (II) and (III) can be used. Examples of lactams of formula (I) which can be used in the present invention include 2-pyrrolidone (γ-butyrolactam), 2-piperidone (δ-valerolactam), ε-caprolactam and laurolactam, each individually or in a mixture. ε-Caprolactam is particularly preferred.

As diols of formula (II) or (III) it is useful to employ ethylene glycol, 1,2- and 1,3-propylene glycol, 1,4-butanediol and also the oligomeric oxyethylene and oxypropylene glycols with degrees of polymerization of from 2 to 20, preferably from 2 to 4. It is also useful to use mixed oligomers with oxyethylene and oxypropylene units. Preference is given to oligooxyethylene and oligooxypropylene glycols having degrees of polymerization from 2 to 4, especially diethylene glycol.

The diol monoethers which can be employed in accordance with the invention include monoetherified diols selected from those set out above. In this case, the alkyl group has 1 to 6, preferably 1 to 4 and, with particular preference, 1 or 2 carbon atoms; specific mention is made of the monomethyl and monoethyl ethers of ethylene glycol and diethylene glycol. The diols and diol monoethers can each be used individually or in a mixture.

Very particular preference is given to modifiers which can be obtained by reacting ε-caprolactam, formaldehyde and diethylene glycol.

The crude mixtures prepared in accordance with the invention, which are preferably used as they are, can be added as modifiers for melamine resins (impregnating resins) in any phase of melamine resin production.

Alternatively, it is useful to separate the N-alkoxymethyllactams VI by a fractional precipitation, for example, and to employ them alone as modifiers.

Any desired amount of the modifier can be added to the melamine. Particularly useful melamine impregnating resin formulations are obtained if the modifiers of the invention are added to melamine resins in a molar ratio of melamine to formaldehyde of from 1 mol:1.4 mol to 1 mol:1.8 mol. The lactam derivatives of the invention, or the product mixtures, are added to the resins to be modified in an amount such that the ratio $m_L/m_{MR}$ of the mass $m_L$ of the lactam derivative (or of the product mixture) to the mass $m_{MR}$ of the melamine resin solid is from 1 to 20%, preferably from 2 to 10%, addition being possible before, during or after the condensation of the resin. In addition to the lactam derivatives of the invention it is also possible to add other modifiers as well, such as butanediol, ε-caprolactam, diethylene glycol, phenoxy-ethanol or sugars, in proportions by mass of in total of from 2 to 20%, preferably from 5 to 15%, based on the mass of the solids of the modified resin.

The resulting resins modified in accordance with the invention (melamine impregnating resin formulations) have a highly uniform quality, good stability on storage and are outstandingly suitable for impregnating decorative paper which can be processed conventionally on all common types of machines both by the short-cycle process for producing upgraded chipboard panels and by the CPL (continuously pressed laminates) process or HPL (high pressure laminates) process for producing laminates. The resulting surfaces are highly resistant both chemically and mechanically, exhibit high elasticity, are free from cracks, and display a high and uniform gloss.

In particular, when the melamine impregnating resin formulations of the invention are used, compared with prior art resins, there are markedly lower emissions when the resinated papers are dried.

The production of decoratively coated woodbase panels using the melamine impregnating resin formulations of the invention takes place by impregnating the paper or fabric web with a melamine resin modified in accordance with the invention and then subjecting said web to conventional further processing (cf. e.g. Ullmanns Enzyklopädie der techn. Chemie, 4th edition, volume 7 (1974), p. 417 f., hereby incorporated by reference in its entirety).

In the examples which follow, as in the text which precedes them, all figures with the unit "%" are proportions by mass unless indicated otherwise. Parts are always by mass. Concentrations in % are proportions by mass of the dissolved substance in the solution, unless stated otherwise. The examples are for illustrative purposes only and do not limit the scope of the invention.

The following measurement methods are employed for characterization:

| | |
|---|---|
| nonvolatiles content | A sample of mass $m_P$ = 2 g is dried at 120° C. in a drying oven for one hour in a glass (G) or aluminum (Al) weighing boat. The mass of the dry residue is $m_T$; $m_{T,G}$ when using glass boats and $m_{T,Al}$ when using aluminum boats. The parameter stated is the mass proportion of the dry residue $W_{T,G} = m_{T,G}/m_P$ (=NVC (glass)) or $W_{T,Al} = m_{T,Al}/m_P$ (=NVC (alu)). |
| water dilutability | deionized water is added slowly at 20° C. to one part of resin having the mass $m_R$ and the volume $V_R$, until there is distinct turbidity. The amount of water required for this is t parts with the mass $m_W$ or the volume $V_W$. The parameter stated is the volume ratio $\psi_{WR} = V_W/V_R$ (t parts by volume of water, 1 part by volume of resin) in cm³/cm³, or the mass ratio $\zeta_{WR} = m_W/m_R$ (t parts by mass of water, 1 part by mass of resin) in g/g. |
| Flow time: | The flow time of a liquid from a flow cup in accordance with DIN 53211 having a 4 mm diameter exit aperture |

EXAMPLES

A. Preparing the Modifiers

Example 1

A 4 l three-necked flask with KPG stirrer, reflux condenser and internal thermometer was charged with 1486 g (14.0 mol) of diethylene glycol, 1584 g (14.0 mol) of ε-caprolactam, 924 g of 91% paraformaldehyde (Granuform®, Degussa, 28.0 mol) and 13.3 g of p-toluenesulfonic acid.H$_2$O (0.070 mol) and this initial charge was heated with stirring to 100° C. over 90 minutes. The reaction mixture was stirred at 100° C. for 30 minutes, during which time it became a solution. The condensation was terminated by cooling the solution to 30° C. and adjusting the pH to 8 with about 11 g of 50% strength sodium hydroxide solution. The finished modifier is of infinite miscibility with water and has the following characteristics:

| | | |
|---|---|---|
| nonvolatiles content (alu) | $w_{T,Al}$ = | 77% |
| pH (20° C.) | | 8.3 |
| Concentration of free formaldehyde (DIN 16 746 A) | | 7.6% |
| Brookfield viscosity (23° C., LV 2, 60 min⁻¹) | | 158 mPa.s |

According to quantitative $^{13}$C-NMR(H$_2$O+10% DMSO), the mixture contains the following species:

| | |
|---|---|
| ε-Caprolactam | 24.1; 30.1; 31.3; 37.0; 43.7; 182.9 ppm. |
| N,N'-Methylenebis-caprolactam | 24.2; 28.9; 30.5; 37.6; 49.7; 58.8; 180.9 ppm. |
| N-(7-Hydroxy-2,5-dioxaheptyl)-caprolactam | 24.3; 29.3; 30.6; 37.9; 50.1; 62.0; 68.6; 71.1; 73.2; 78.3; 181.1 ppm. |
| Diethylene glycol | 61.9; 73.3 ppm. |

Of the ε-caprolactam employed for the reaction, 1% was present as free ε-caprolactam, 42% as N,N'-methylenebiscaprolactam and 24% as N-(7-hydroxy-2,5-dioxaheptyl)caprolactam in the mixture. 33% could not be allocated to any one defined compound.

Of the diethylene glycol employed for the reaction, 24% was present as N-(7-hydroxy-2,5-dioxaheptyl)caprolactam and 49% as free diethylene glycol. 27% could not be allocated to any one defined compound.

Example 2

A 4 l three-necked flask with KPG stirrer, reflux condenser and internal thermometer was charged with 2122 g (20 mol) of diethylene glycol, 2263 g (20 mol) of ε-caprolactam, 1320 g of 91% paraformaldehyde (Granuform®, Degussa, 40 mol) and 171 g of p-toluenesulfonic acid $H_2O$ (0.90 mol) and this initial charge was heated with stirring to 100° C. over 30 minutes. The reaction mixture was stirred at 100° C. for 10 minutes, during which time it became a solution. The condensation was terminated by cooling the solution to 30° C. and adjusting the pH to 8 with about 105 g of 50% strength sodium hydroxide solution.

Of the ε-caprolactam employed for the reaction, according to $^{13}$C-NMR, 1% was present as free ε-caprolactam, 50% as N,N'-methylenebiscaprolactam and 23% as N-(7-hydroxy-2,5-dioxaheptyl)caprolactam in the mixture. 26% could not be allocated to any one defined compound.

Example 3

A 0.5 l three-necked flask with KPG stirrer, reflux condenser and internal thermometer was charged with 212 g (2.0 mol) of diethylene glycol, 226 g (2.0 mol) of ε-caprolactam, 66 g of 91% paraformaldehyde (Granuform® Degussa, 2.0 mol) and 0.80 g (10 mmol) of 50% strength sodium hydroxide solution and this initial charge was stirred at 100° C. for 30 minutes. Then 19 g (0.10 mol) of p-toluenesulfonic acid.$H_2O$ were added and stirring was continued at 100° C. for 10 minutes. The condensation was terminated by cooling the solution to 3° C. and adjusting the pH to 8 with about 9 g (0.11 mol) of 50% strength sodium hydroxide solution.

Of the ε-caprolactam employed for the reaction, according to $^{13}$C-NMR, 5% was present as free ε-caprolactam, 65% as N,N'-methylenebiscaprolactam and 22% as N-(7-hydroxy-2,5-dioxaheptyl)caprolactam in the mixture; 8% could not be allocated to any one defined compound. 47% of the diethylene glycol employed was in free form.

Example 4

The procedure is as for Example 3. Following addition of the p-toluenesulfonic acid, the reaction mixture was heated to an internal temperature of 140° C. over a period of 2 hours, during which time a total of 23 g of water were removed by distillation. The condensation was terminated by cooling to 30° C. and adjusting the pH to 9 with about 9 g (0.11 mol) of 50% strength sodium hydroxide solution.

Of the ε-caprolactam employed for the reaction, according to $^{13}$C-NMR, 6% was present as free ε-caprolactam, 70% as N,N'-methylenebiscaprolactam and 24% as N-(7-hydroxy-2,5-dioxaheptyl)caprolactam in the mixture. 52% of the diethylene glycol employed was in free form.

Example 5

Modifiers were prepared in analogy to Example 1 using 1,4-butanediol and, respectively, polyethylene glycol 200 (PEG 200). The batches were stirred at 100° C. for 30 minutes, cooled and neutralized with an amount of sodium hydroxide solution equivalent to the amount of acid. The amounts employed and characteristics of the resulting modifiers are given in the table below:

| | | | Characteristics | | |
|---|---|---|---|---|---|
| Example | Composition | | NVC (glass) | pH (1:1) | Flow time |
| 5A | 339.5 g (3.0 mol) | ε-caprolactam | 89% | 8.3 | 29 s |
| | 270.4 g (3.0 mol) | 1,4-butanediol | | | |
| | 99.0 g (3.0 mol) | 91% paraformaldehyde | | | |
| | 2.85 g (0.015 mol) | p-toluenesulfonic acid.$H_2O$ | | | |
| 5B | 339.5 g (3.0 mol) | ε-caprolactam | 83% | 6.7 | 28 s |
| | 270.4 g (3.0 mol) | 1,4-butanediol | | | |
| | 198.0 g (6.0 mol) | 91% paraformaldehyde | | | |
| | 2.85 g (0.015 mol) | p-toluenesulfonic acid.$H_2O$ | | | |
| 5C | 282.9 g (2.5 mol) | ε-caprolactam | 92% | 5.8 | 30 s |
| | 500.0 g (2.5 mol) | polyethylene glycol 200 | | | |
| | 82.5 g (2.5 mol) | 91% paraformaldehyde | | | |
| | 2.38 g (0.013 mol) | p-toluenesulfonic acid.$H_2O$ | | | |
| 5D | 282.9 g (2.5 mol) | ε-caprolactam | 90% | 5.4 | 37 s |
| | 500.0 g (2.5 mol) | polyethylene glycol 200 | | | |
| | 165.0 g (5.0 mol) | 91% paraformaldehyde | | | |

-continued

| Example | Composition | | Characteristics | | |
|---|---|---|---|---|---|
| | | | NVC (glass) | pH (1:1) | Flow time |
| | 2.38 g (0.013 mol) | p-toluenesulfonic acid.H$_2$O | | | | pH (1:1): pH of the sample diluted with deionized water in a ratio of 1:1 by mass.

B. Preparing the Impregnating Resins

Example 6

A 1 liter three-necked flask with KPG stirrer, reflux condenser and internal thermometer was charged with 219.3 g of deionized water, 88 g of the modifier from Example 1 and 395 g (5.1 mol) of 39% formaldehyde. Then 0.4 g (5 mmol) of 50% strength sodium hydroxide solution and, subsequently, 454 g (3.6 Mol) of melamine were added. The pH (23° C.) of the reaction mixture was 9.9. The reaction mixture was heated to reflux temperature (about 103° C.) and stirred at reflux for 10 minutes, then cooled to 85° C. and condensed to a water dilutability $\psi_{WR}$=2 (1 part by volume of resin to 2 parts by volume of deionized water). The condensation was terminated by cooling to 30° C. The resin obtained had a content by mass $w_{T,Al}$ of nonvolatiles of 59%.

Example 7

A 50 l reactor with stirrer, reflux condenser and internal thermometer was charged with 9.3 kg of deionized water, 40 kg of the modifier from Example 2 and 17.1 kg (223 mol) of 39% formaldehyde. Then 17.4 g (0.22 mol) of 50% strength sodium hydroxide solution and, subsequently, 19.6 kg (156 mol) of melamine were added. The pH (23° C.) of the reaction mixture was 9.6. The reaction mixture was heated to reflux temperature (about 103° C.) and stirred at reflux for 10 minutes, then cooled to 85° C. and condensed to a water dilutability of 1 part by volume of resin to 1.9 parts by volume of deionized water. The condensation was terminated by cooling to 30° C. The resin obtained had the following characteristics:

| NVC (glass) | $w_{T,G}$ = 60.6% |
|---|---|
| Density (20° C.) | ρ = 1247 kg/m³ |
| pH | 9.7 |
| Discharge time | 18.0 s |
| Water dilutability | $\zeta_{WR}$ = 1.6 g/g |
| Storage life | about 4 weeks |

Example 8

Impregnating resins were prepared in accordance with Example 6 using the modifiers from Example 5. The composition of the reaction mixtures and the characteristics of the resins are given in the table below:

| Example | Composition | | Characteristics | | | |
|---|---|---|---|---|---|---|
| | | | NVC (alu) | $\zeta_{WR}$ | pH | Discharge time |
| 8A | 184.0 g | deionized water | 59% | 1.7 g/g | 9.2 | 15 s |
| | 72.4 g | modifier from Example 5A | | | | |
| | 2.24 ml | 2 N sodium hydroxide soln. | | | | |
| | 369.8 g | 39.1% strength aqueous formaldehyde | | | | |
| | 403.5 g | melamine | | | | |
| 8B | 197.3 g | deionized water | 59% | 1.4 g/g | 9.2 | 17 s |
| | 82.5 g | modifier from Example 5B | | | | |
| | 2.24 ml | 2 N sodium hydroxide soln. | | | | |
| | 346.4 g | 39.1% strength aqueous formaldehyde | | | | |
| | 403.5 g | melamine | | | | |
| 8C | 179.4 g | Deionized water | 60% | 1.6 g/g | 9.1 | 16 s |
| | 68.7 g | Modifier from Example 5C | | | | |
| | 2.24 ml | 2 N sodium hydroxide soln. | | | | |
| | 378.0 g | 39.1 strength aqueous formaldehyde | | | | |
| | 403.5 g | melamine | | | | |
| 8D | 188.1 g | deionized water | 60% | 1.6 g/g | 9.2 | 17 s |
| | 75.3 g | modifier from Example 5D | | | | |
| | 2.24 ml | 2 N sodium hydroxide soln. | | | | |
| | 362.9 g | 39.1 strength aqueous formaldehyde | | | | |
| | 403.5 g | melamine | | | | |

Comparative Example 1

A 50 l reactor with stirrer, reflux condenser and internal thermometer was charged with 8.3 kg of deionized water, 1.5 kg of ε-caprolactam, 1.4 kg of diethylene glycol and 19.1 kg (249 mol) of 39% formaldehyde. Then 17.4 g (0.22 mol) of 50% strength sodium hydroxide solution and, subsequently, 19.6 kg (156 mol) of melamine were added. The pH (23° C.) of the reaction mixture was 9.7. The reaction mixture was heated to reflux temperature (about 103° C.) and stirred at reflux for 10 minutes, then cooled to 85° C. and condensed to a water dilutability $\psi_{WR}$=1.9 (1 part by volume of resin to 1.9 parts by volume of deionized water). The condensation was terminated by cooling to 30° C.

The resin obtained had the following characteristics:

| (NVC (glass), 2 g, 1 h 120° C.) | $w_{T,G}$ = 60.7% |
|---|---|
| Density (20° C.) | ρ = 1245 kg/m³ |
| pH | 9.6 |
| Discharge time | 17.5 s |
| Water dilutability | $\zeta_{WR}$ = 1.5 g/g |
| Storage life | about 5 weeks |

Comparative Example 2

A 1 l three-necked flask with KPG stirrer, reflux condenser and internal thermometer was charged with 145 g of deionized water and 444 g (5.77 mol) of 39% formaldehyde.

Then 2.5 ml of 2 N (5 mmol) sodium hydroxide solution and, subsequently, 454 g (3.6 mol) of melamine were added. The pH (23° C.) of the reaction mixture was 9.4.

The reaction mixture was heated to reflux temperature (about 103° C.) and stirred at reflux for 10 minutes, then cooled to 85° C. and condensed to a water dilutability $\psi_{WR}=1.9$ (1 part by volume of resin to 1.9 parts by volume of deionized water). The condensation was terminated by cooling to 30° C. The resin obtained had the following characteristics:

| | |
|---|---|
| NVC (Alu) | $w_{T,Al}$ = 58.8% |
| pH | 9.4 |
| water dilutability | $\zeta_{WR}$ = 1.3 g/g |
| storage life | 4 days |

Comparative Example 3

In relation to the resins of Example 8, the corresponding resins modified with the simple modifiers 1,4-butanediol or polyethylene glycol 200 (molar mass about 200 g/mol) and ε-caprolactam, for purposes of comparison. The procedure is as for Comparative Example 1; the composition of the reaction mixtures, and the characteristics, are given in the table below:

| Comparative Example | Composition | | NVC (alu) | $\zeta_{WR}$ | pH | Discharge time |
|---|---|---|---|---|---|---|
| 3A Comparison with Example 8A and B | 171.1 g<br>34.5 g<br>27.4 g<br>2.24 ml<br>393.2 g<br>403.5 g | deionized water<br>ε-caprolactam<br>1,4-butanediol<br>2 N sodium hydroxide soln.<br>39.1% strength aqueous formaldehyde<br>melamine | 60% | 1.9 g/g | 9.3 | 16 s |
| 3B Comparison with Example 8C and D | 171.1 g<br>22.4 g<br>39.6 g<br>2.24 ml<br>393.2 g<br>403.5 g | deionized water<br>ε-caprolactam<br>polyethylene glycol 200<br>2 N sodium hydroxide soln.<br>39.1% strength aqueous formaldehyde<br>melamine | 60% | 1.6 g/g | 9.2 | 16 s |

C. Investigating the Emissions Behavior

Investigation 1

The smoking behavior of films impregnated with the resins from Example 7 and Comparative Example 1 was assessed qualitatively. The overall composition of the two resins (melamine, formaldehyde, εcaprolactam and diethylene glycol) is the same. The resins were adjusted with an acidic amine salt (p-toluenesulfonic acid/morpholine) to a turbidity time (T time) of from 5 to 5½ minutes at 100° C. These liquid impregnating formulations were used to impregnate decorative paper which was then dried in a drying cabinet at 180° C. The smoking behavior was monitored at intervals of a minute. The results are set out in the table below:

| Resin | T time 100° C. min | Smoking behavior at 180° C. after | | | |
|---|---|---|---|---|---|
| | | 1 min | 2 min | 3 min | 4 min |
| Example 7 | 5½ | nothing found | nothing found | nothing found | slight smoking |
| Comparative Example 1 | 5 | nothing found | nothing found | slight smoking | distinct smoking |

Investigation 2

The emissions of ε-caprolactam (capro) and diethylene glycol (DEG) from the resins from Example 7, Comparative Example 1 and Comparative Example 2 were investigated by means of GC analysis. For this purpose, the resin solutions were injected directly at a block temperature of 120° C. or 160° C. respectively. The results obtained are set out in the tables below:

GC analysis at 120° C. (volatile fractions based on resin solution):

| Resin | Modification | Capro | DEG | Capro + DEG |
|---|---|---|---|---|
| Example 7 | in accordance with the invention with modifier from Ex. 2 | 0.8% | 0.6% | 1.4% |
| Comp. Example 1 | Caprolactam and diethylene glycol | 2.5% | 2.3% | 4.8% |
| Comp. Example 2 | unmodified | <0.1% | <0.1% | <0.1% |

GC analysis at 160° C. (volatile fractions based on resin solution):

| Resin | Modification | Capro | DEG | Capro + DEG |
|---|---|---|---|---|
| Example 7 | in accordance with the invention with modifier from Ex. 2 | 0.4% | 1.9% | 1.3% |
| Comp. Example 1 | Caprolactam and diethylene glycol | 1.9% | 2.6% | 4.5% |
| Comp. Example 2 | unmodified | <0.1% | | <0.1% |

By using the impregnating resin of the invention from Example 7, comprising the modifier of the invention from Example 2, it is possible to reduce markedly the emissions of ε-caprolactam and diethylene glycol in comparison to the impregnating resin from Comparative Example 1 which is modified with the simple modifiers ε-caprolactam and diethylene glycol.

Investigation 3

The smoking behavior of films impregnated with the resins from Example 8 and Comparative Example 3 was assessed qualitatively. The overall composition of the resins (melamine, formaldehyde, εcaprolactam and 1,4-butanediol from Example 8A, 8B and Comparative Example 3A, and the overall composition of the resins (melamine, formaldehyde, ε-caprolactam and polyethylene glycol 200) from Example 8C, 8D and Comparative Example 3B, is the same in each case. The resins were adjusted with an acidic amine salt p-toluenesulfonic acid/morpholine) to a turbidity time (T time) of from 5 to 5½ minutes at 100° C. These liquid impregnating formulations were used to impregnate decorative paper which was then dried in a drying cabinet at 180° C. The smoking behavior was monitored at intervals of a minute. The results are set out in the table below:

|  | Smoking behavior at 180° C. after: | | | |
| --- | --- | --- | --- | --- |
| Resin | 1 min | 2 min | 3 min | 4 min |
| Example 8A | nothing found | nothing found | Slight | distinct |
| Example 8B | nothing found | nothing found | Slight | distinct |
| Comparative Example 3A | nothing found | slight | Distinct | severe |
| Example 8C | nothing found | nothing found | Nothing found | distinct |
| Example 8D | nothing found | nothing found | nothing found | distinct |
| Comparative Example 3B | nothing found | nothing found | distinct | severe |

By using the impregnating resins of the invention from Example 8 it is possible to achieve a marked reduction in smoking relative to the prior art (Comparative Example 3).

D. Performance Testing

Investigation 4

The impregnating resins from Example 7 and Comparative Example 1 were subjected to performance testing for use in the short-cycle process. For this purpose, the resin solutions were adjusted with an acidic amine salt (p-toluenesulfonic acid/morpholine) to a turbidity time of about 5 minutes. The decorative papers (PWA, A-60 S, 80 g/m$^2$) impregnated with these resin solutions were dried in a drying cabinet and then pressed onto chipboard panels (60 s, 160° C. at the paper, 3 MPa [=30 bar], press plate HS-18). The results of the test are given in the table below:

|  | Testing the coated chipboard panel | | | | |
| --- | --- | --- | --- | --- | --- |
|  | Melamine film | | | | Tempering acc. to DIN 68765, 4.6 |
| Resin | Resin content | Residual moisture | Surface | Kiton test 2h | Over-curing |
| Example 7 | 60% | 6.0% | nothing found | 2–3 | nothing found | nothing found |
| Comparative Example 1 | 58% | 6.1% | nothing found | 2 | nothing found | nothing found |

Kiton Test
Testing of surfaces treated with MF resin
Solution I
  1000 ml of H$_2$O
  20 ml of H$_2$SO$_4$
  20 ml of 2% strength aqueous solution of ®Lissamine Red B
  (manufacturer: ICI)

A "glass eye" (dome) filled with solution I is applied to the sample and allowed to act at room temperature for 2 hours. Thereafter, the test site is cleaned thoroughly with water and assessed using a 6-point color scale.

The stages of coloring range from stage 1: no staining=overcuring, to stage 6: dark violet staining=complete undercuring.

In the case of treated chipboard panels, the aim should be to achieve cures of stage 2 or 2–3 (good, good-moderate).

There are no differences in terms of short-cycle performance between the resin of the invention from Example 7 and the prior art resin from Comparative Example 1.

Investigation 5

The impregnating resins from Example 7 and Comparative Example 1 were subjected to performance testing for use in the CPL process. For this purpose, the resin solutions were adjusted with an acidic amine salt (p-toluenesulfonic acid/morpholine) to a turbidity time of about 5 minutes. The decorative papers (PWA, A-60 S, 80 g/m$^2$, resin add on about 60%, residual moisture about 6%) or core ply papers (sodium kraft, 135 g/m$^2$, resin add on about 50%, residual moisture about 6.7%) impregnated with these resin solutions were dried in a drying cabinet and then pressed to give laminates consisting of one decorative film ply and 3 core plys (35 s, 175° C., 3.5 MPa [=35 bar], press plate HS-18). The results of the test are given in the table below:

|  | Testing of the laminates | | | | |
| --- | --- | --- | --- | --- | --- |
| Resin | Surface | Kiton test 2h | Steam test* 60 min | Boil test# 2h | Boil test# 6h | Post-forming+ |
| Example 7 | nothing found | 3 | nothing found | nothing found | nothing found | nothing found |
| Comp. Ex. 1 | nothing found | 2 | nothing found | nothing found | nothing found | nothing found |

*in accordance with DIN-EN 438, section 24
in accordance with DIN-EN 438, section 7
+in accordance with DIN-EN 438, section 20

There are no differences in terms of laminate production performance between the resin of the invention from Example 7 and the prior art resin from Comparative Example 1.

German Application 197 44 942.5 filed Oct. 10, 1997 (the priority document of the present application) is hereby incorporated by reference in its entirety.

Although only a few exemplary embodiments of this invention have been described in detail above, those skilled in the art will readily appreciate that many modifications are possible in the exemplary embodiments without materially departing from the teachings and advantages of this invention. Accordingly, all such modifications are intended to be included within the scope of this invention.

We claim:
1. A compound of the formula VI

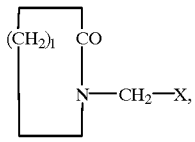 (VI)

where X is —(OCH$_2$—CR$^1$H)$_m$—OR$^2$, and R$^1$ and R$^2$ independently of one another are hydrogen or a linear or branched alkyl radical having 1 to 6 carbon atoms, l is 5 and m is 1 to 20,
or where X is —O—(CH$_2$)$_n$—OR$^3$, and R$^3$ is hydrogen or a linear or branched alkyl radical having 1 to 6 carbon atoms and n is 2 to 8,
obtained by reacting a lactam of the formula I

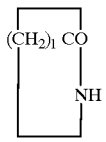 (I)

where l is as defined above, with formaldehyde and one or more hydroxyl-containing compounds selected from diols or diol monoethers of formula II H(—O—CH$_2$—CR$^1$H)$_m$—OR$^2$ (II), where R$^1$, R$^2$ and m are as defined above, and diols or diol monoethers of formula III HO—(CH$_2$)$_n$—OR$^3$ (III)

where R$^3$ and n are as defined above,
wherein the reacting comprises
reacting from 1 to 4 mol of formaldehyde and from 0.5 to 6 mol of the hydroxy containing compound with one another per mole of the lactam of the formula I.

2. A method of using a compound of the formula VI as claimed in claim 1, comprising adding it to a melamine resin or adding it during the preparation of a melamine resin.

3. A melamine impregnating resin formulation comprising or prepared from a compound of the formula VI as claimed in claim 1 as modifier in a proportion by mass of from 1 to 20%, based on the mass of the solid melamine resin.

4. A compound of the formula VI

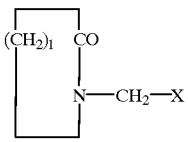 (VI)

where X is —(OCH$_2$—CR$^1$H)$_m$—OR$^2$, and R$^1$ and R$^2$ in each case independently of one another are hydrogen or a linear or branched alkyl radical having 1 to 6 carbon atoms, l is 5 and m is 1 to 20,
or where X is —O—(CH$_2$)$_n$—OR$^3$ and R$^3$ is hydrogen or a linear or branched alkyl radical having 1 to 6 carbon atoms and n is 2 to 8.

* * * * *